United States Patent [19]

Ogi et al.

[11] Patent Number: 5,767,302

[45] Date of Patent: Jun. 16, 1998

[54] HIGH-PURITY TI COMPLEXES, METHODS FOR PRODUCING THE SAME AND BST FILM-FORMING LIQUID COMPOSITIONS

[75] Inventors: Katsumi Ogi; Hiroto Uchida; Atsushi Itsuki; Kazuo Wakabayashi, all of Omiya, Japan

[73] Assignee: Mitsubishi Materials Corporation, Tokyo, Japan

[21] Appl. No.: 688,774

[22] Filed: Jul. 31, 1996

[30] Foreign Application Priority Data

Jul. 31, 1995 [JP] Japan .................................. 7-194874
Jul. 31, 1995 [JP] Japan .................................. 7-194875

[51] Int. Cl.⁶ .............................. C07F 7/28; C04B 35/00; C04B 35/46
[52] U.S. Cl. .................................. 556/54; 556/1; 501/1; 501/138
[58] Field of Search .............................. 556/54, 1; 501/1, 501/138

[56] References Cited

U.S. PATENT DOCUMENTS

| | | | |
|---|---|---|---|
| 5,349,073 | 9/1994 | Horn et al. .................................. | 556/54 |
| 5,654,456 | 8/1997 | Scott et al. .................................. | 556/28 |
| 5,679,815 | 10/1997 | Kirlin et al. .................................. | 556/42 |

FOREIGN PATENT DOCUMENTS 2264119  8/1993  United Kingdom.

OTHER PUBLICATIONS

Jpn. J. Appl. Phys. vol 33 (1994) pp. 5129–5134, Part 1, No. 9B, Sep. 1994 "Step Coverage and Electrical Properties of $(Ba,Sr)TiO_3$ Films Prepared by Liquid Source Chemical Vapor Deposition Using $TiO(DPM)_2$,". Takaai Kawahara, Mikio Yamamuka, Tetsuro Makita, Jiro Naka, Akimasa Yuuki, Noboru Mikami and Kouichi Ono.

Primary Examiner—Porfirio Nazario-Gonzalez
Attorney, Agent, or Firm—Oblon, Spivak, McClelland, Maier & Neustadt, P.C.

[57] ABSTRACT

Two types of high-purity Ti complexes, $[TiO(DPM: dipivaloylmethane)_2]_2$ and $cis$-$Ti(O$-$t$-$Bu)_2(DPM)_2$, and BST film-forming liquid compositions comprising solutions of either of the two types of high-purity Ti complexes and $Ba(DPM)_2$ and/or $Sr(DPM)_2$ in organic solvents can be used to form BST films. Crystals of the former complex are produced by adding purified water to a solution of $TiCl_2(DPM)_2$ in an organic solution, adding an alkali chemical to the solution to adjust the pH to 6.0–8.0 to thereby produce turbidity, and separating the organic layer which is then washed with water and heated to reflux. Crystals of the latter complex is produced by adding HDPM to a solution of $Ti(O$-$t$-$Bu)_4$ in an organic solvent, and heating the solution to reflux.

20 Claims, 5 Drawing Sheets

HIGH-PURITY TI COMPLEXES, METHODS FOR PRODUCING THE SAME AND BST FILM-FORMING LIQUID COMPOSITIONS

BACKGROUND OF THE INVENTION

Field of the Invention

The present invention relates to high-purity Ti complexes suitable as raw materials for forming Ti-containing metal oxide thin films by chemical vapor deposition (CVD), which are useful as dielectric films, semiconductor films, optical thin films, surface-reinforcing films, thin-film catalysts, etc., methods for producing them, and BST film-forming liquid compositions.

DESCRIPTION OF THE RELATED ART

Raw materials which have long been used for forming Ti-containing, dielectric thin films by CVD, such as strontium titanate, barium strontium titanate (BST) and lead zirconate titanate, further include a variety of metal alkoxide compounds and TiDPM ("DPM" refers to dipivaloylmethanato radical: $(CH_3)_3$-C-CO-CH-CO-C-$(CH_3)_3$) complexes which are used in combination with alkoxide compounds and DPM complexes of Ba, Sr, Zr, etc.

Of these CVD raw materials, Japanese Unexamined Patent Application Disclosure HEI 5-271253 titled "High-purity Titanium Complexes and Method for Producing the Same" discloses the TiDPM complexes $Ti(R^1)_2(R^2)_2$ wherein $R^1$ is a β-diketone such as acetylacetone, 3,5-heptanedione or dipivaloylmethane, and $R^2$ is an alkoxy group such as methoxy, ethoxy, isopropoxy (hereunder, represented as "-o-i-Pr"), n-propoxy or n-butoxy, and a method of producing them. Here, only $Ti(O-i-Pr)_2(DPM)_2$ is referred to as an embodiment of the TiDPM complexes in Japanese Unexamined Patent Application Disclosure HEI 5-271253.

When $Ti(O-i-Pr)_2(DPM)_2$ is used as a raw material for forming BST films by CVD in combination with $Ba(DPM)_2$ and $Sr(DPM)_2$, since the heat decomposition temperature of $Ti(O-i-Pr)_2(DPM)_2$ is as low as 270° C. (255°–290° C.) as compared with the heat decomposition temperatures of $Ba(DPM)_2$ and $Sr(DPM)_2$, 350°–410° C., $Ti(O-i-Pr)_2(DPM)_2$ tends to decompose in the vapor phase during formation of the films, increasing the probability of adsorption of the vapor-phase decomposition products on the substrates. This leads to the disadvantage of poor step coverage during formation of the films on substrates with uneven surfaces.

$Ti(O-n-Bu)_2(DPM)_2$ with an n-butoxy group (-O-n-Bu) introduced as the alkoxy group, is known as well, but this material, having only a somewhat higher decomposition temperature of 280° C. (260°–310° C.), has not succeeded in improving the step coverage during formation of films by thermal CVD on substrates with uneven surfaces.

In addition, although $TiCl_2(DPM)_2$ [heat decomposition temperature: 330° C. (320°–340° C.)] is known as a satisfactorily heat-stable material as well, this material presents a problem when used as a raw material for forming BST films in that the chloride ions (Cl-) present in the molecule are incorporated into the films as impurity chlorine.

Known methods for feeding CVD raw materials for formation of metal oxide films of composite compositions include a method in which metal compounds used as the raw materials are prepared as a solution in an organic solvent and fed into a vaporizer as a liquid, in which they are heated to vaporization together with the solvent and fed to a CVD film-forming chamber as a gas. According to this method, however, the Ti compounds, $Ti(O-i-Pr)_2(DPM)_2$ and $Ti(O-n-Bu)_2(DPM)_2$, tend to react with $Ba(DPM)_2$ and $Sr(DPM)_2$ in the solution, forming complexes of higher molecular weight, thus presenting the problem of impaired vaporizing properties. Also, according to the method, when the Ti compounds contain OR groups as impurities, $Ba(DPM)_2$ and $Sr(DPM)_2$, being highly reactive with the OR groups, react with the OH groups to lower the vaporizing properties, producing the problem of increasing the amount of the residue inside the vaporizer and the amount of precipitation of decomposition products on the gas piping, shower head and elsewhere, and also making it difficult to control the film composition.

SUMMARY OF THE INVENTION

An object of the present invention is to provide high-purity Ti complexes which are free from impurity problems due to their outstanding high purities.

Another object of the present invention is to provide high-purity Ti complexes which are free from poor step coverage problems caused by decomposition in vapor phase due to their high heat decomposition temperatures.

Another object of the present invention is to provide high-purity Ti complexes which are free from poor vaporizing property problems caused by formation of complexes of higher molecular weight.

Another object of the present invention is to provide methods of producing the high-purity Ti complexes and BST film-forming liquid compositions employing the high-purity Ti complexes.

The high-purity Ti complex according to a first embodiment of the present invention is the high-purity Ti complex represented by the following chemical formula (I):

$$[TiO(DPM)_2]_2 \qquad (I)$$

wherein DPM is dipivaloylmethato radical.

$[TiO(DPM)_2]_2$ has a decomposition temperature of 325° C. (300°–350°) which is higher than that of the conventional $Ti(O-i-Pr)_2(DPM)_2$, and is almost the same as the decomposition temperatures of $Ba(DPM)_2$ and $Sr(DPM)_2$. Accordingly, adsorption of the vapor-phase decomposition products on substrates is prevented, improving the step coverage.

In addition, since $[TiO(DPM)_2]_2$ can be purified to a high purity with an OH group content of 0.1% by weight or less and a chlorine content of 5 ppm or less, high-purity Ti oxide thin films can be formed without presenting the impurity contamination problem.

The high-purity Ti complex can be easily produced by a method according to a second embodiment of the present invention, whereby purified water is added to a solution of dichlorobis(dipivaloylmethanato)-titanium complex, $TiCl_2(DPM)_2$, in an organic solvent, an alkali chemical is added to the solution while stirring to adjust the pH of the aqueous layer to 6.0–8.0, thereby causing turbidity, and then separating the organic layer which is washed with purified water and heated to reflux to yield crystals.

The BST film-forming liquid composition according to a third embodiment of the present invention is a solution of the high-purity Ti complex according to the present invention and bis(dipivaloylmethanato)-barium complex, $Ba(DPM)_2$, and/or bis (dipivaloylmethanato)-strontium complex, $Sr(DPM)_2$, in an organic solvent.

Since the high-purity Ti complex used as the Ti material has a significantly low OR-group content and a very high purity, its vaporizing property is not impaired even when used in combination with Ba(DPM)₂ and/or Sr(DPM)₂. Thus, BST films of any desired composition can be efficiently formed without presenting the problem of increasing the amount of the residue inside the vaporizer and the amount of precipitation of the decomposition products on the gas piping, shower head and elsewhere.

The high-purity Ti complex according to a fourth embodiment of the present invention is the high-purity Ti complex, cis-Ti(O-t-Bu)₂(DPM)₂, represented by the following structural formula (II):

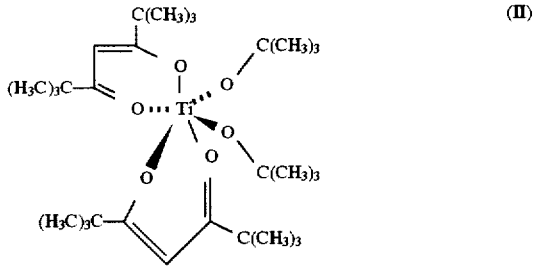

cis-Ti(O-t-Bu)₂(DPM)₂ has a heat decomposition temperature of 315° C. (300°–340° C.) which is higher than that of the conventional Ti(O-i-Pr)₂(DPM)₂ or Ti(O-i-Bu)₂(DPM)₂, and is almost the same as the heat decomposition temperatures of Ba(DPM)₂ and Sr(DPM)₂. Accordingly, the adsorption of the vapor-phase decomposition products on the substrates is prevented, improving the step coverage.

In addition, since cis-Ti(O-t-Bu)₂(DPM)₂ can be purified to a high purity with an OH-group content of 0.1% by weight or less, and a chlorine content of 5 ppm or less, high-purity Ti oxide thin films can be formed without presenting the impurity contamination problem.

Furthermore, since cis-Ti(O-t-Bu)₂(DPM)₂ has retarded reactivity with Ba(DPM)₂ and/or Sr(DPM)₂ in solution due to the presence of the bulky alkoxy groups (O-t-Bu) as compared with the (O-n-Bu) and (O-i-Pr) of Ti(O-i-Pr)₂(DPM)₂ and Ti(O-n-Bu)₂(DPM)₂, there are no problems resulting from the reaction of the Ti compound with the Ba and/or Sr compound, such as the formation of complexes of high molecular weight which could impair the vaporizing property.

The high-purity Ti complex can be produced by a method of producing the high-purity Ti complex according to a fifth embodiment of the present invention, whereby dipivaloylmethane is added to a solution of tetra(tert-butoxy)-titanium in an organic solvent which is then heated to reflux at 100° C. or higher to remove the residual water and the OH groups by azeotropy, and then concentrated to yield crystals.

The BST film-forming liquid composition according to a sixth embodiment of the present invention is a solution of the high-purity Ti complex according to the present invention and bis(dipivaloylmethanato)-barium complex, Ba(DPM)₂, and/or bis (dipivaloylmethanato)-strontium complex, Sr(DPM)₂, in an organic solvent.

Since the high-purity Ti complex used as the Ti material has a significantly low OR-group content and a very high purity, and further is free from complex formation problems as described above, its vaporizing property is not impaired even when used in combination with Ba(DPM)₂ and/or Sr(DPM)₂. Thus, BST films of any desired composition can be efficiently formed without presenting the problem of increasing the amount of the residue inside the vaporizer and the amount of precipitation of the decomposition products on the gas piping, shower head and elsewhere.

DETAILED DESCRIPTION OF THE INVENTION

Figure 1:
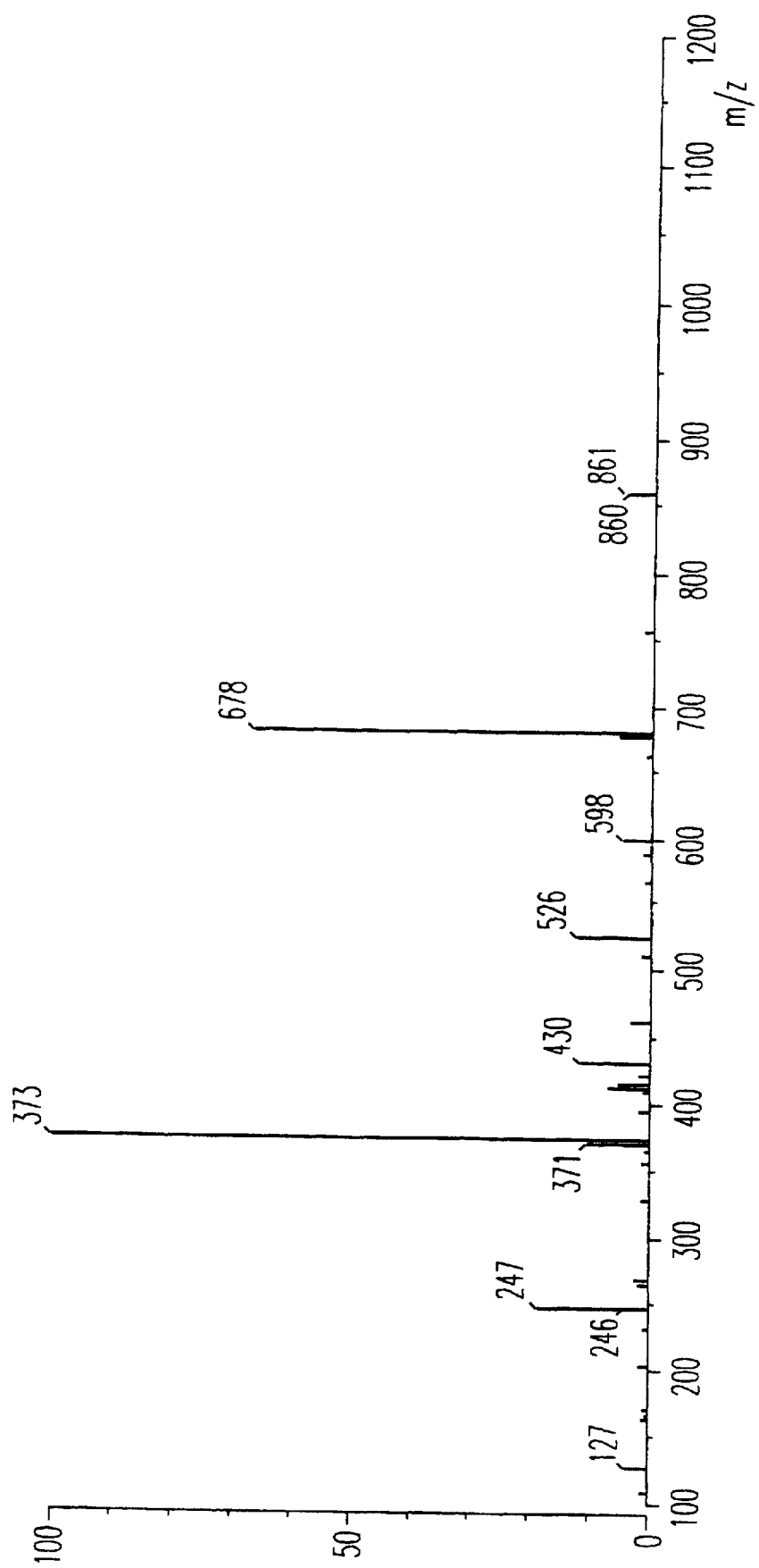
FIG. 1 is a graph showing results of mass spectrometric analysis of crystals of [TiO(DPM)₂]₂ produced in Example 1.

The present invention will now be explained in detail. An explanation will be first given regarding the high-purity Ti complex according to the first embodiment of the present invention and a method of producing it.

The high-purity Ti complex according to the first embodiment of the present invention, as expected from the results of the analysis in Example 1 given later, is (dipivaloylmethanato)-titanium complex of a structure with one Ti atom surrounded by a total of six oxygen atom ligands, that is, the oxygen atoms of the carboxy groups of two dipivaloylmethane molecules and two oxygen atoms shared with another Ti atom.

In order to produce the Ti complex, TiCl₂(DPM)₂ is first dissolved in an organic solvent, such as an aromatic hydrocarbon, e.g. toluene, xylene or mesitylene, or an aliphatic hydrocarbon such as pentane or n-hexane, to a concentration of 1.0–40% by weight, and purified water is added to the resulting solution. Then an alkali chemical, such as aqueous ammonia, is added dropwise while vigorously stirring, until the pH of the aqueous layer changes to a weakly alkaline value of 6.0–8.0, preferably 7.0–7.5, at which turbidity is produced. Here, the amount of the purified water to be added to the solution of TiCl₂(DPM)₂ is preferably on the order of 5–20 times by volume that of the solution of TiCl₂(DPM)₂. In addition, the concentration of the aqueous ammonia used is preferably about 0.1–5N. Other alkali chemicals suitable for adjusting the pH of the aqueous layer are well known to those of ordinary skill in the art, such as NaOH, KOH, alkylammonium hydroxides and solutions thereof, although these are less preferred.

The starting material TiCl₂(DPM)₂ is well known to those of ordinary skill in the art.

The organic layer is then separated off, washed with purified water and then heated to reflux in an oil bath at a temperature which is typically 10°–50° C. higher than the boiling point of the organic solvent used, to remove the residual water and the OH groups by azeotropy, and the solution is concentrated to yield crystals.

By recrystallizing these crystals from an aprotic organic solvent such as toluene, xylene or mesitylene and purifying the recrystallized crystals through a repetition of sublimation of the solvent under reduced pressure, high-purity [TiO(DPM)₂]₂ can be prepared which has an OH-group content of 0.1% by weight or less and a residual chlorine content of 5 ppm or less.

When the OH-group content of the [TiO(DPM)₂]₂ exceeds 0.1% by weight, its vaporizing property is impaired when used in combination with another raw material which is highly reactive with the OR groups of Ba(DPM)$_2$ and/or Sr(DPM)$_2$ to prepare a liquid composition for forming composite metal oxide films. This presents the problem of increasing the amount of residue inside the vaporizer and the amount of precipitation of the decomposition products on the gas piping, shower head and elsewhere, and varying the film composition.

Ba(DPM)$_2$ and Sr(DPM)$_2$ are well known to those or ordinary skill in the art.

On the other hand, with a residual chlorine content of over 5 ppm, the purity of the resulting Ti oxide film is reduced.

In summary, the high-purity Ti complex according to the first embodiment of the present invention preferably has an OH-group content of 0.1% by weight or less and a chlorine content of 5 ppm or less.

The high-purity Ti complex according to the first embodiment of the present invention, having a high heat decomposition temperature and having a significantly lowered content of impurities, such as OH-groups and residual chlorine, produces the following effects:

1) During formation of films by CVD, the amount of adsorption of the decomposition products of the Ti complex in the vapor phase on substrates is reduced, improving the step coverage during the film formation;

2) High-purity Ti oxide films with excellent electrical characteristics and free from impurity contamination are formed; and 3) Even when used in combination with another raw material which is highly reactive with the OR groups of Ba(DPM)$_2$, Sr(DPM)$_2$ or the like, the vaporizing property of the raw material is not impaired. Thus, Ti-containing composite metal oxide films of desired compositions are formed through easy control of the film compositions, without presenting the problem of increasing the amount of the residue inside the vaporizer and the amount of precipitation of the decomposition products on the gas piping, shower head and elsewhere.

Accordingly, use of the high-purity Ti complex as a raw material for forming BST films by CVD allows formation of dielectric thin films having 1 Gbyte or more memory, with fine and elaborated configurations.

The complex described above, [TiO(DPM)$_2$]$_2$, can be easily produced according to a method of producing the high-purity Ti complex according to a second embodiment of the present invention.

The high-purity Ti complex according to the fourth embodiment of the present invention will now be explained.

The high-purity Ti complex according to the fourth embodiment of the present invention, as expected from the results of the analysis in Example 5 given later, is cis-bis (dipivaloylmethanato)-di(tert-butoxy)-titanium complex, cis-Ti(O-t-Bu)$_2$(DPM)$_2$, having a structure with one Ti atom to which the oxygen atoms of the carboxy groups of two dipivaloylmethane molecules and two tert-butoxy groups are bonded in the cis arrangement.

In order to produce the Ti complex, tetra-(tert-butoxy) titanium is first dissolved in an organic solvent, such as an aromatic hydrocarbon, e.g. toluene, xylene or mesitylene, or an aliphatic hydrocarbon such as pentane or n-hexane, to a concentration of 1–70% by weight, and dipyvaloylmethane, HDPM, is added to the resulting solution in an amount 2.0–2.5 molar times that of the Ti(O-t-Bu)$_4$. The mixture is heated to reflux in an oil bath at a temperature of typically 100° C. or higher, or at a temperature which is 10°–50° C. higher than the boiling point of the organic solvent used, to remove the residual water and the OH groups by azeotropy, and the solution is concentrated to yield crystals.

Ti(O-t-Bu)$_4$ is well known to those of ordinary skill in the art.

By recrystallizing these crystals from an aprotic, dry organic solvent such as toluene, xylene or mesitylene and purifying the recrystallized crystals through a repetition of sublimation of the solvent under reduced pressure, high-purity cis-Ti(O-t-Bu)$_2$(DPM)$_2$ can be prepared which has an OH-group content of 0.1% by weight or less and a residual chlorine content of 5 ppm or less.

When the OH-group content of the cis-Ti(O-t-Bu)$_2$(DPM)$_2$ exceeds 0.1% by weight, the vaporizing property is impaired when used in combination with another raw material which is highly reactive with the OR groups of Ba(DPM)$_2$ and/or Sr(DPM)$_2$ to prepare a liquid composition for forming composite metal oxide films. This presents the problem of increasing the amount of the residue inside the vaporizer and the amount of precipitation of the decomposition products on the gas piping, shower head and elsewhere, and varying the film composition.

On the other hand, with a residual chlorine content of over 5 ppm, the purity of the resulting Ti oxide film is reduced.

In summary, the high-purity Ti complex according to the fourth embodiment of the present invention preferably has an OH-group content of 0.1% by weight or less and a chlorine content of 5 ppm or less.

The high-purity Ti complex according to the fourth embodiment of the present invention, having a high heat decomposition temperature, having a significantly lowered content of impurities, such as OH groups and residual chlorine, and further being free from the problem of forming complexes with Ba(DPM)$_2$, Sr(DPM)$_2$ etc., produces the following effects:

1) During formation of films by CVD, the amount of adsorption of the decomposition products of the Ti complex in vapor phase on substrates is reduced, improving the step coverage during the film formation;

2) High-purity Ti oxide films with excellent electrical characteristics and free from impurity contamination are formed; and 3) Ti-containing composite metal oxide films of desired compositions are formed through easy control of the film compositions, without presenting the problem of forming complexes with Ba(DPM)$_2$, Sr(DPM)$_2$, etc., without impairing the vaporizing property of another raw material which is used in combination with the Ti complex and is highly reactive with the OH groups and thus without presenting the problem of increasing the amount of the residue inside the vaporizer and the amount of precipitation of the decomposition products on the gas piping, shower head and elsewhere.

Accordingly, use of the high-purity Ti complex as a raw material for forming BST films by CVD allows formation of dielectric thin films of 1 Gbyte or more memory, having fine and elaborated configurations.

The high-purity Ti complex described above, cis-Ti(O-t-Bu)$_2$(DPM)$_2$, can be easily produced according to a method of producing the high-purity Ti complex according to a fifth embodiment of the present invention.

The liquid composition for forming BST films according to the present invention is a solution of [TiO(DPM)$_2$]$_2$ or cisTi(O-t-Bu)$_2$(DPM)$_2$, according to the present invention, and Ba(DPM)$_2$ and/or Sr(DPM)$_2$ in an organic solvent, prepared so as to provide a desired film composition.

Here, the organic solvent preferably is one or more selected from the group consisting of pyridine, lutidine and tetrahydrofuran (THF), and more preferably [TiO(DPM)$_2$]$_2$ or cis-Ti(O-t-Bu)$_2$(DPM)$_2$, and Ba(DPM)$_2$ and/or Sr(DPM)$_2$ are dissolved in such an organic solvent to a total concentration of 1–20% by weight.

In the context of the invention, lutidine may be any isomer of dimethylpyridine (2,3-lutidine, 2,4-lutidine, 2,5-lutidine, 2,6-lutidine, 3,4-lutidine, 3,6-lutidine, etc.) or mixtures thereof.

The BST film-forming liquid composition prepared in this way is a solution of the Ti, Ba and/or Sr materials in the same organic solvent which is free from the problem of impaired vaporization, and this solution can be steadily subjected to a method of feeding CVD raw materials, whereby the solution is fed to a vaporizer in which the solution is heated to vaporization together with the solvent, and fed to a CVD film-forming chamber as a gas.

Significantly, the high-purity Ti complexes according to the present invention, [TiO(DPM)$_2$]$_2$ and cis-Ti(O-t-Bu)$_2$(DPM)$_2$, can each used as a CVD raw material in the solid state, directly or after being dissolved in an organic solvent, together with another metal compound, if necessary, as described above, in a conventional manner.

Having generally described this invention, a further understanding can be obtained by reference to certain specific examples which are provided herein for purposes of illustration only and are not intended to be limiting unless otherwise specified.

EXAMPLE 1

Synthesis of high-purity [TiO(DPM)$_2$]$_2$

To 200 ml of a solution of TiCl$_2$(DPM)$_2$ in toluene (concentration: 30% by weight) was added 1,500 ml of purified water to which was then slowly added dropwise aqueous ammonia (1.2% by weight) while vigorously stirring, until the pH of the aqueous layer changed from neutral to a weakly alkaline value. The point at which the solution began to become turbid was determined to be the endpoint. The toluene layer was then separated and washed well with purified water, the solution was heated to reflux in an oil bath at a temperature of 130°–150° C. to remove the residual water and the OH groups by azeotropy, and was then concentrated to yield white crystals. The crystals were recrystallized from toluene and then purified by sublimation at 190° C. and under reduced pressure.

The resulting crystals were identified by $^1$H-NMR (C$_6$D$_6$+ d-THF), mass spectrometric analysis and elemental analysis. The results were as follows:

$^1$H-NMR: δ, 5.9331 (2H, —CH); 1.563 (36H, C(CH$_3$)$_3$)

Elemental analysis: Calculated, Ti=11.12%; C=61.39%; H=8.90%; o=18.59%. Found, Ti=11.08%; C=61.45%; H=8.64%; o=18.59%.

Mass spectrometric analysis: The molecular ion was confirmed to have a peak at M/z=860, as shown in FIG. 1.

The analytical results described above suggest that the resulting [TiO(DPM)$_2$]$_2$ has the following structure:

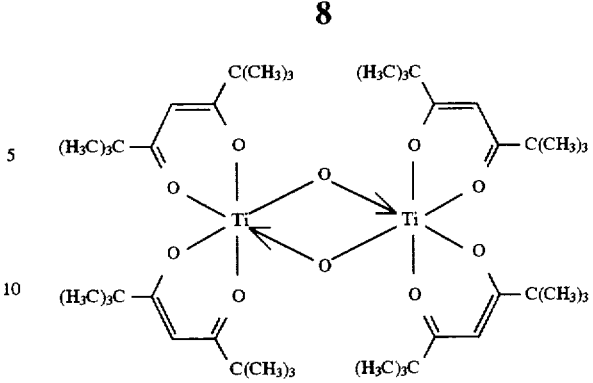

Here, it has been confirmed that the residual Cl content is <1 ppm according to elemental analysis of the crystals of [TiO(DPM)$_2$]$_2$, and an OH-group content of <0.1% by weight according to IR analysis.

Figure 2:
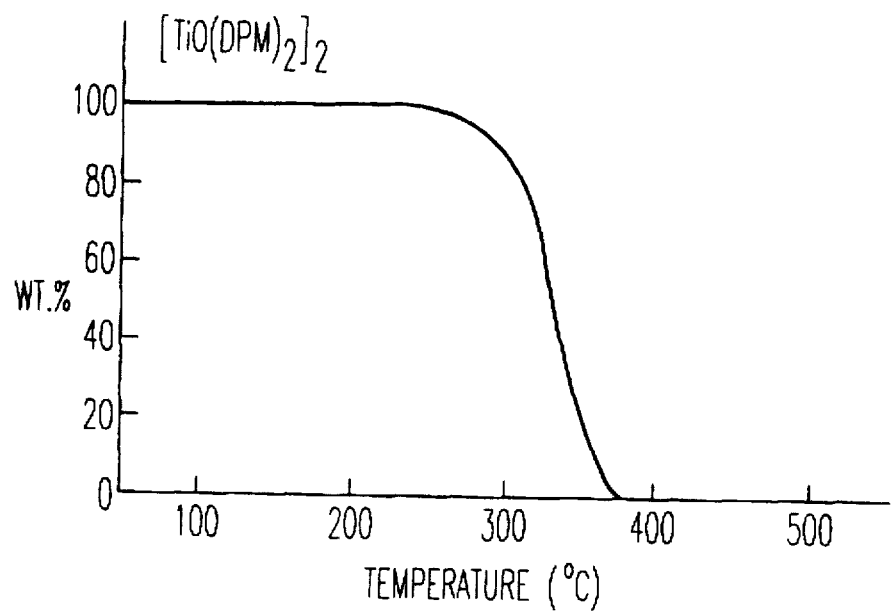
FIG. 2 is a graph showing results of TG (thermogravimetric) analysis of crystals of [TiO(DPM)₂]₂ produced in Example 1.

The [TiO(DPM)$_2$]$_2$ crystals were subjected to TG analysis under a stream of Ar and at a temperature-rise rate of 10° C./min., with the results shown in FIG. 2, which demonstrate that the [TiO(DPM)$_2$]$_2$ began to vaporize at 200° C., and 100% vaporization was achieved at 360° C.

Separately, the [TiO(DPM)$_2$]$_2$ crystals were sealed in an Al vessel and then subjected to DTA (Differential Thermal Analysis) analysis under a stream of Ar and at a temperature-rise rate of 10° C./min.; the heat decomposition temperature was confirmed to be 325° C. (300°–350° C.).

EXAMPLE 2

Test on film formation by CVD

[TiO(DPM)$_2$]$_2$ crystals having residual chlorine contents of 4 ppm, 6 ppm, 200 ppm and 3000 ppm, respectively, were obtained in the same manner as in Example 1, except that the amount of dropwise addition of aqueous ammonia was reduced to change the pH of the aqueous layer to a weakly acidic value. These [TiO(DPM)$_2$]$_2$ crystals and the [TiO(DPM)$_2$]$_2$ crystals with a residual chlorine content of <1 ppm, which were obtained in Example 1, were used as the Ti materials, respectively, in combination with Ba(DPM)$_2$ and Sr(DPM)$_2$ to form BST (Ba$_{0.7}$Sr$_{0.3}$Ti$_{0.1}$) films by CVD under the following film-forming conditions:

Film-forming conditions
CVD apparatus: Substrate heating-type CVD apparatus
Reaction gas: O$_2$
Carrier gas: Ar
Vaporization temp.: (TiO(DPM)$_2$)$_2$=180° C. Ba(DPM)$_2$= 200° C. Sr(DPM)$_2$=190° C.
Film-forming pressure: 2.0 Torr
Substrate: Pt/Ti electrode
Substrate temp.: 600° C.
Film thickness: 1000 Å

An Au electrode was formed on each of the obtained BST films by vapor deposition, and the electrical characteristics were evaluated with the results shown in Table 1.

TABLE 1

| No. | 1 | 2 | 3 | 4 | 5 |
|---|---|---|---|---|---|
| Residual Cl content (ppm) | <1 | 4 | 6 | 200 | 3,000 |
| Dielectric const. | 200 | 220 | 180 | 170 | 170 |

TABLE 1-continued

| No. | 1 | 2 | 3 | 4 | 5 |
|---|---|---|---|---|---|
| Dielectric loss | 0.01 | 0.02 | 0.07 | 0.07 | 0.07 |
| Leakage current (3 V) | $5 \times 100^{-5}$ | $8 \times 10^{-5}$ | $11 \times 10^{-7}$ | $3 \times 10^{-7}$ | $8 \times 10^{-5}$ |
| Remarks | Example | | | Compar. Example | |

EXAMPLE 3

Test on step coverage during CVD

Figure 7:
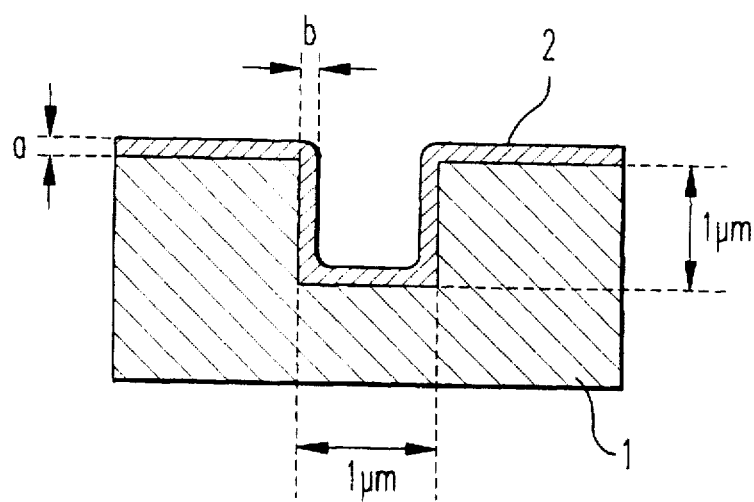
FIG. 7 is a cross sectional view illustrative of the method of evaluating step coverage which is used in Examples 3 and 7.

The $Ti(O-i-Pr)_2(DPM)_2$ described in Japanese Unexamined Patent Application Disclosure HEI 5-271253 and the high-purity $[TiO(DPM)_2]_2$ produced in Example 1 were used separately to form a film 2 of $TiO_2$ on a trenched substrate 1 having the cross section illustrated in FIG. 7, by thermal CVD under the following conditions to evaluate the step coverage on the basis of the ratio a/b, that is, the ratio of the film thickness "a" to the film thickness "b" of the film 2 of $TiO_2$ formed by CVD, as shown in FIG. 7, with the results shown in Table 2. The step coverage is evaluated to improve as the ratio a/b approaches one.

Film-forming conditions

Vaporization temp.: $[TiO(DPM)_2]_2=180°$ C. $Ti(O-i-Pr)_2(DPM)_2=140°$ C.
Film-forming pressure: 2.0 Torr
Substrate temp.: 600° C.

Figure 3:
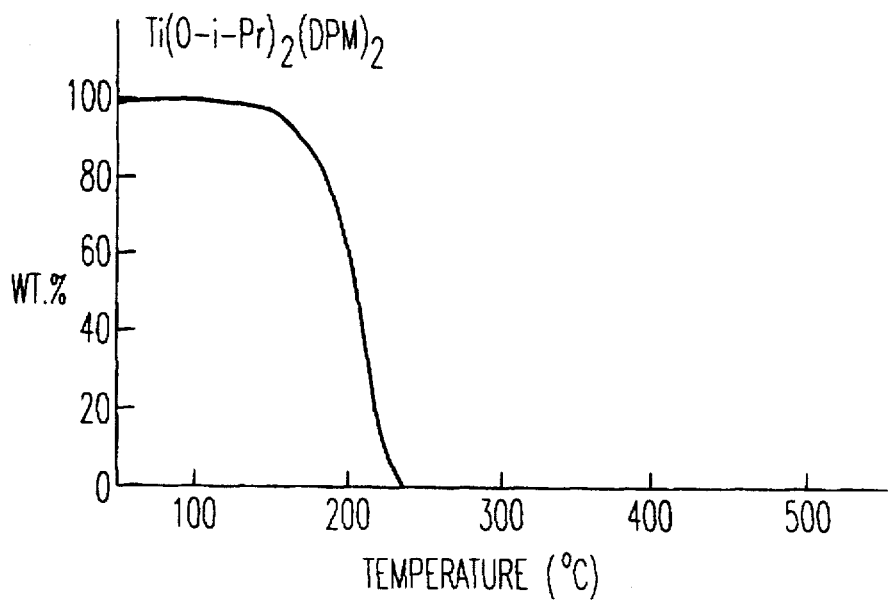
FIG. 3 is a graph showing results of TG analysis of Ti(O-i-Pr)₂(DPM)₂.

The $Ti(O-i-Pr)_2(DPM)_2$ was analyzed by TG and DTA in the same manner as in Example 1, with the results shown in FIG. 3 and Table 2.

TABLE 2

| No. | Ti complex | Vaporization temp. (°C.) | Heat decomposition temp. (°C.) | Step coverage (a/b) | Remarks |
|---|---|---|---|---|---|
| 6 | $[TiO(DPM)_2]_2$ | 200–360 | 325 (300–350) | 1.0 | Example |
| 7 | $Ti(O-i-Pr)_2(DPM)_2$ | 130–240 | 270 (255–290) | 1.2 | Compar. Example |

EXAMPLE 4

Evaluation of the vaporizing properties of BST solutions $[TiO(DPM)_2]_2$ crystals having OH-group contents of 0.2%, 1% and 2%, by weight, respectively, were produced in the same manner as in Example 1, but omitting the dehydration step by azeotropy using toluene as the solvent. These $[TiO(DPM)_2]_2$ crystals, and the high-purity $[TiO(DPM)_2]_2$ with an OH-group content of <0.1% which was produced in Example 1, were each dissolved in dry solvents listed in Table 3 together with $Ba(DPM)_2$ and $Sr(DPM)_2$ at a compositional ratio (molar ratio) of Ba:Sr:Ti=0.5:0.5:1. The resulting solutions were concentrated under reduced pressure to precipitate solids were evaluated by TG under Ar for their vaporizing ties, with the results shown in Table 3.

TABLE 3

| No. | OH-group content of $[TiO(DPM)_2]_2$ (wt. %) | Solvent | Vaporization temp. (°C.) | Vaporization rate (%) | Remarks |
|---|---|---|---|---|---|
| 8 | <0.1 | Dry THF | ~450 | 93 | Example |
| 9 | <0.1 | Dry lutidine | ~450 | 97 | |
| 10 | <0.1 | Dry pyridine | ~450 | 98 | |
| 11 | <0.1 | Dry (THF/lutidine)* | ~450 | 97 | |
| 12 | 0.2 | Dry THF | ~450 | 80 | Compar. Example |
| 13 | 1 | Dry THF | ~450 | 78 | |
| 14 | 2 | Dry THF | ~450 | 70 | |

*THF: lutidine = 50:50 (volumetric ratio)

EXAMPLE 5

Synthesis of high-purity cis-$Ti(O-t-Bu)_2(DPM)_2$

To a solution of $Ti(O-t-Bu)_4$ in toluene (concentration: 30% by weight) was added HDPM in an amount two molar times that of the $Ti(O-t-Bu)_4$, the resulting solution was heated to reflux in an oil bath at a temperature of 130°–150° C. to remove the dual water and the OH groups by azeotropy, and was then concentrated to yield white crystals. The crystals were crystallized from toluene and then purified by sublimation at 190° C. and under reduced pressure.

The resulting crystals were identified by $^1H$-NMR ($C_6D_6$+ d-THF), mass spectrometric analysis and elemental analysis. The results were as follows:

$^1H$-NMR: δ, 1.1092 (9H, $C(CH_3)_3$, DPM); 1.2682 (9H, $OC(CH_3)_3$); 1.4056 (9H, $C(CH_3)_3$, DPM)

Elemental analysis: Calculated, Ti=8.54%; C=64.27%; H=10.07%; o=17.12%; Cl=0%. Found, Ti=8.59%; C=64.21%; H=10.05%; o=17.15%; Cl<1 ppm.

Figure 4:
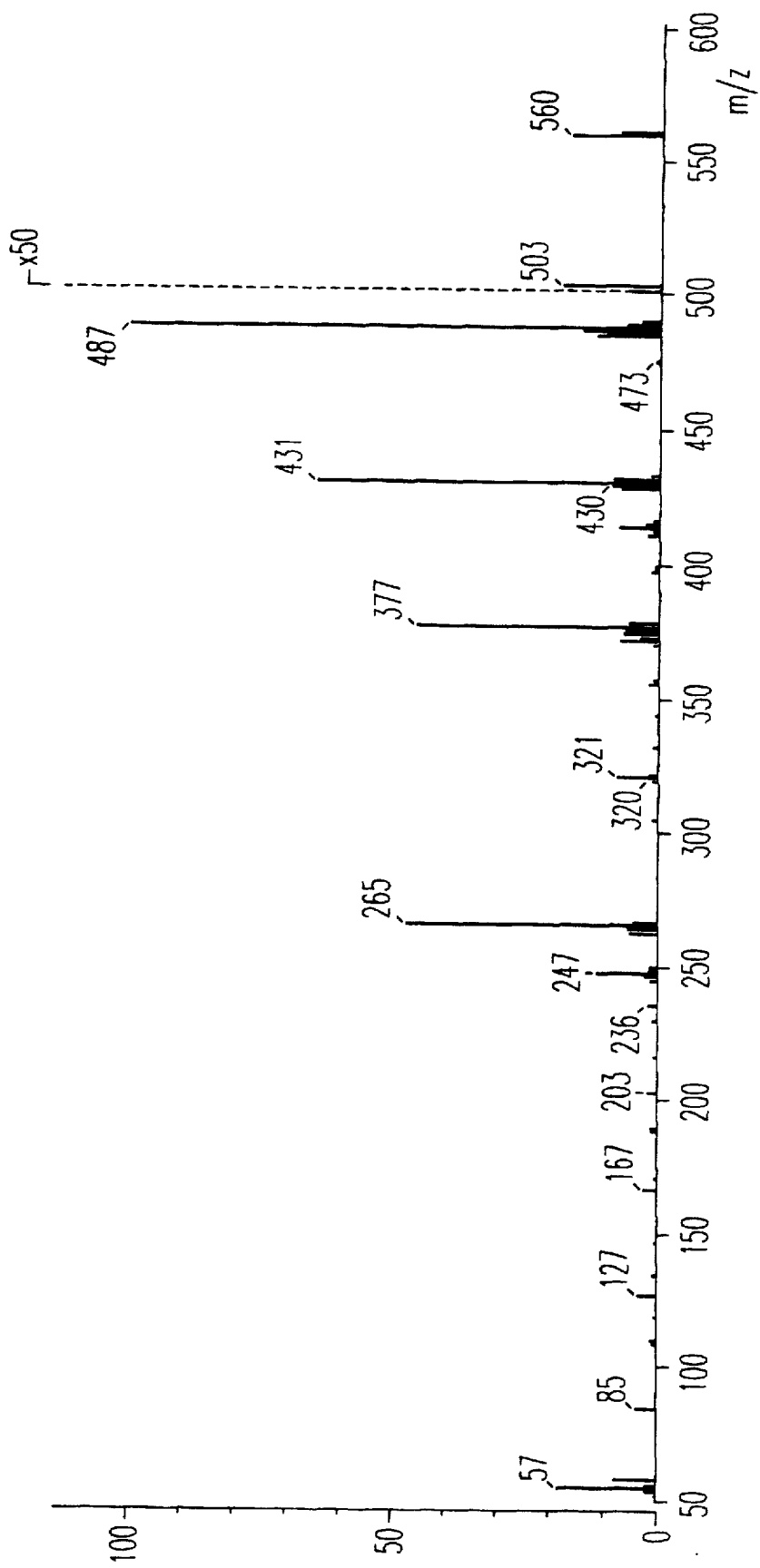
FIG. 4 is a graph showing results of mass spectrometric analysis of crystals of cis-Ti(O-t-Bu)₂(DPM)₂ produced in Example 5.

Mass spectrometric analysis: The molecular ion was confirmed to have a peak at M/z=560, as shown in FIG. 4.

The analytical results described above suggest that the resulting cis-$Ti(O-t-Bu)_2(DPM)_2$ has the following structure:

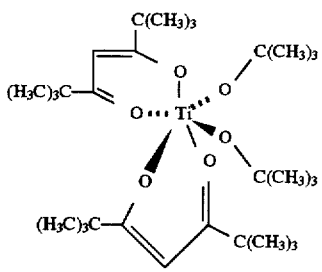

Here, it was confirmed that the yielded crystals of cisTi$(O-t-Bu)_2(DPM)_2$ had a residual Cl content of <1 ppm according to elemental analysis and an OH-group content of <0.1% by weight according to IR analysis.

Figure 5:
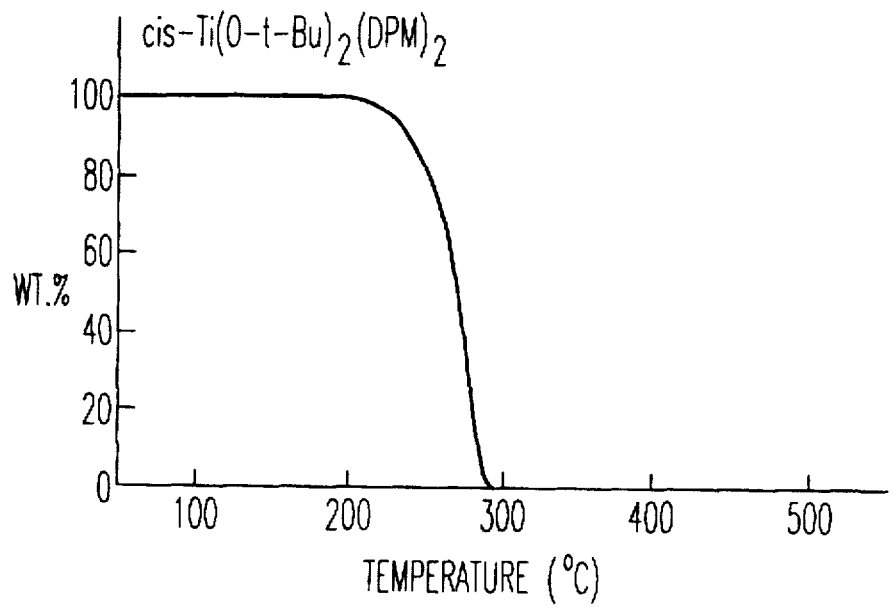
FIG. 5 is a graph showing results of TG analysis of crystals of cis-Ti(O-t-Bu)₂(DPM)₂ produced in Example 5.

The cis-$Ti(O-t-Bu)_2(DPM)_2$ crystals were subjected to TG analysis under a stream of Ar and at a temperature-rise rate of 10° C./min., with the results shown in FIG. 5, which demonstrate that the cis-$Ti(O-t-Bu)_2(DPM)_2$ began to vaporize at 175° C., and 100% vaporization was achieved at 280° C.

Separately, the cis-$Ti(O-t-Bu)_2(DPM)_2$ crystals were sealed in an Al vessel and then subjected to DTA analysis under a stream of Ar and at a temperature-rise rate of 10° C./min.; the heat decomposition temperature was confirmed to be 315° C. (300°–340° C.).

EXAMPLE 6

Test on film formation by CVD cis-Ti(O-t-Bu)$_2$(DPM)$_2$ crystals having residual chlorine contents of 4 ppm, 6 ppm, 50 ppm and 200 ppm, respectively, were obtained in the same manner as in Example 5, but using Ti(O-t-Bu)$_4$ having a chlorine content of 5–300 ppm as the starting material. These cis-Ti(O-t-Bu)$_2$(DPM)$_2$ crystals, and the cis-Ti(O-t-Bu)$_2$(DPM)$_2$ crystals with a residual chlorine content of <1 ppm which were obtained in Example 5, were used as the Ti materials, respectively, in combination with Ba(DPM)$_2$ and Sr(DPM)$_2$ to form BST (Ba$_{0.7}$Sr$_{0.3}$Ti$_{0.1}$) films by CVD under the following film-forming conditions:

Film-forming conditions
CVD apparatus: Substrate heating-type CVD apparatus
Reaction gas: O$_2$
Carrier gas: Ar
Vaporization temp.: cis-Ti(O-t-Bu)$_2$(DPM)$_2$=160° C. Ba(DPM)$_2$=200° C. Sr(DPM)$_2$=190° C.
Film-forming pressure: 2.0 Torr
Substrate: Pt/Ti electrode
Substrate temp.: 600° C.
Film thickness: 1000 Å

An Au electrode was formed on each of the obtained BST films by vapor deposition, and the electrical characteristics were evaluated with the results shown in Table 4.

TABLE 4

| No. | 15 | 16 | 17 | 18 | 19 |
|---|---|---|---|---|---|
| Residual Cl content (ppm) | <1 | 4 | 6 | 50 | 200 |
| Dielectric const. | 225 | 220 | 195 | 178 | 171 |
| Dielectric loss | 0.01 | 0.01 | 0.07 | 0.07 | 0.07 |
| Leakage current (3 V) | 5 ×10$^{-8}$ | 8 ×10$^{-8}$ | 8 ×10$^{-7}$ | 6 ×10$^{-7}$ | 3 ×10$^{-7}$ |
| Remarks | Example | | | Compar. Example | |

EXAMPLE 7

Test on step coverage during CVD

The Ti(O-i-Pr)$_2$(DPM)$_2$ described in Japanese Unexamined Patent Application Disclosure HEI 5-271253, Ti(O-n-Bu)$_2$(DPM)$_2$, and the high-purity cis-Ti(O-t-Bu)$_2$(DPM)$_2$ produced in Example 5, were used separately to form a film 2 of TiO$_2$ on a trenched substrate 1 having the cross section illustrated in FIG. 7, by thermal CVD under the following conditions to evaluate the step coverage on the basis of the ratio a/b, that is, the ratio of the film thickness "a" to the film thickness "b" of the film 2 of TiO$_2$ formed by CVD, as shown in FIG. 7, with the results shown in Table 5. The step coverage is evaluated to improve as the a/b approaches one.

Film-forming conditions
Vaporization temp.: cis-Ti(O-t-Bu)$_2$(DPM)$_2$=160° C.
Ti(O-i-Pr)$_2$(DPM)$_2$=140° C.
Ti(O-n-Bu)$_2$(DPM)$_2$=180° C.
Film-forming pressure: 2.0 Torr
Substrate temp.: 600° C.

Figure 6:
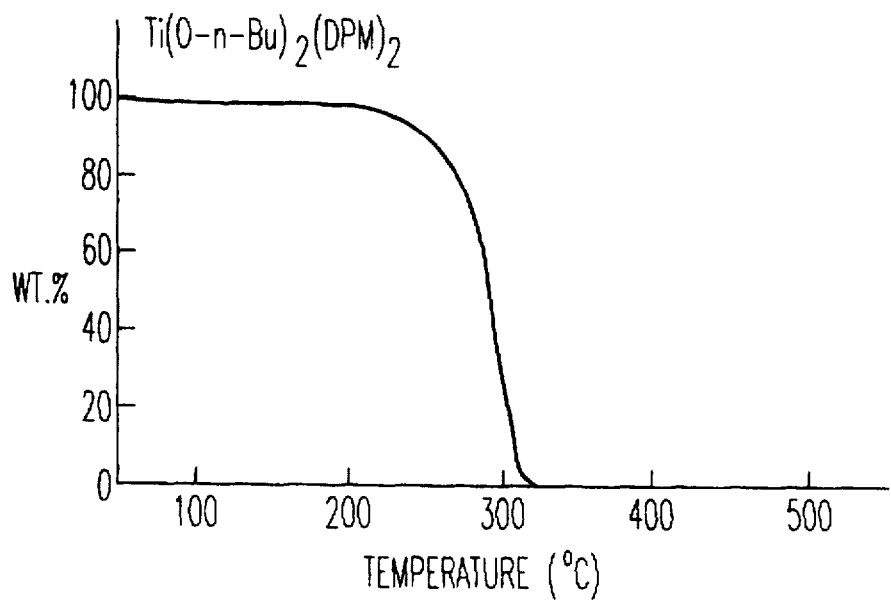
FIG. 6 is a graph showing results of TG analysis of Ti(O-n-Bu)₂(DPM)₂.

The Ti(O-i-Pr)$_2$(DPM)$_2$ and the Ti(O-n-Bu)$_2$(DPM)$_2$ were separately analyzed by TG and DTA in the same manner as in Example 5, with the results shown in FIGS. 3 and 6, and Table 5 (the analytical results of the Ti(O-i-Pr)$_2$(DPM)$_2$ were the same as reported in Example 3 described above).

TABLE 5

| No. | Ti complex | Vaporization temp. (°C.) | Heat decomposition temp. (°C.) | Step coverage (a/b) | Remarks |
|---|---|---|---|---|---|
| 20 | cis-Ti(O-t-Bu)$_2$(DPM)$_2$ | 175–280 | 315 (300–340) | 1.0 | Example |
| 21 | Ti(O-i-Pr)$_2$(DPM)$_2$ | 130–240 | 270 (255–290) | 1.2 | Compar. Example |
| 22 | Ti(O-n-Bu)$_2$(DPM)$_2$ | 180–310 | 280 (260–310) | 1.2 | |

EXAMPLE 8

Evaluation of the vaporizing properties of BST solutions cis-Ti(O-t-Bu)$_2$(DPM)$_2$ crystals having OH-group contents of 0.2%, 0.8% and 2%, by weight, respectively, were produced in the same manner as in Example 5, except that benzene was used as the solvent, and the heating was carried out at a temperature of 100° C. or 80° C. These cis-Ti(O-t-Bu)$_2$(DPM)$_2$ crystals, and the high-purity cis-Ti(O-t-Bu)$_2$(DPM)$_2$ crystals, with an OH-group content of <0.1% which were produced in Example 5, were each dissolved in dry solvents listed in Table 6 together with Ba(DPM)$_2$ and Sr(DPM)$_2$ at a compositional ratio (molar ratio) of Ba:Sr:Ti= 0.5:0.5:1, and the resulting solutions were each concentrated under reduced pressure to precipitate solids which were evaluated by TG under Ar for their vaporizing properties, with the results shown in Table 6.

TABLE 6

| No. | OH-group content of cis-Ti(O-t-Bu)$_2$(DPM)$_2$ (wt. %) | Solvent | Vaporization temp. (°C.) | Vaporization rate (%) | Remarks |
|---|---|---|---|---|---|
| 23 | <0.1 | Dry THF | ~450 | >95 | Example |
| 24 | <0.1 | Dry lutidine | ~450 | >95 | |
| 25 | <0.1 | Dry pyridine | ~450 | >95 | |
| 26 | <0.1 | Dry (THF/lutidine)* | ~450 | >95 | |
| 27 | 0.2 | Dry THF | ~450 | 85 | Compar. Example |
| 28 | 0.8 | Dry THF | ~450 | 83 | |
| 29 | 2 | Dry THF | ~450 | 80 | |

*THF: lutidine = 50:50 (volumetric ratio)

EXAMPLE 9

Evaluation of the vaporizing properties of BST solutions cis-Ti(O-t-Bu)$_2$(DPM)$_2$ of Example 5, which had an OH-group content of <0.1% and Ti(O-t-Bu)$_2$(DPM)$_2$ as the Comparative Example, were dissolved in dry solvents, respectively, together with Ba(DPM)$_2$ and Sr(DPM)$_2$ at a compositional ratio (molar ratio) of Ba:Sr:Ti=0.7:0.3:1, and the resulting respective solutions were analyzed by TG in the same manner as in Example 8, with the results shown in Table 7.

TABLE 7

| No. | Ti compound | Solvent | Vaporization temp. (°C.) | Vaporization rate (%) | Remarks |
|---|---|---|---|---|---|
| 30 | cis-Ti(O-t-Bu)$_2$(DPM)$_2$ | Dry (THF/lutidine)* | ~600 | 100 | Example |
| 31 | Ti(O-t-Bu)$_2$(DPM)$_2$ | Dry lutidine | ~600 | 80 | Compar. Example |

*THF: lutidine = 50:50 (volumetric ratio)

The priority documents of the parent application,
HEI 7-194875, and HEI 7-194874, both filed in Japan on Jul. 31, 1995, are hereby incorporated by reference.

Obviously, additional modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A Ti complex:

$$(TiO(DPM)_2)_2,$$

wherein DPM is (CH$_3$)$_3$-C-CO-CH-CO-C-(CH$_3$)$_3$.

2. The Ti complex of claim 1, wherein said complex has an OH-group content of at most 0.1% by eight, and a chlorine content of at most 5 ppm.

3. A method of making (TiO(DPM)$_2$)$_2$ comprising:
   making a solution comprising dichlorobis (dipivaloylmethanato) titanium complex and and organic solvent,
   adding purified water to the solution, thereby forming a mixture comprising an aqueous layer and an organic solution layer, and
   adjusting the pH of the aqueous layer of the mixture to 6.0–8.0, to produce turbidity.

4. The method of claim 3, further comprising separating an organic layer of the mixture, then washing the organic layer with purified water, and heating to yield crystals.

5. The method of claim 3, wherein the organic solvent is selected from the group consisting of aromatic hydrocarbons and aliphatic hydrocarbons, the solution has a concentration of the dichlorobis (dipivaloylmethanato)-titanium complex of 1.0–40% by weight, and the purified water is added to the solution in a volume 5–20 times that of the solution.

6. The method of claim 3, wherein said pH is adjusted by adding 0.1–5N aqueous ammonia while stirring and the pH of the aqueous layer is adjusted to 7.0–7.5.

7. The method of claim 4, wherein the heating is to a temperature of 10°–50° C. higher than the boiling point of the organic solvent, thereby removing the residual water and the OH groups by azeotropy, and concentrating the organic solvent to yield crystals.

8. The method of claim 4, wherein the crystals are recrystallized from an aprotic solvent selected from the group consisting of toluene, xylene and mesitylene.

9. A liquid composition comprising:
   a solution of the Ti complex of claim 1, at least one of bis(dipivaloylmethanato)-barium complex and bis (dipivaloylmethanato)-strontium complex, and
   an organic solvent.

10. The liquid composition of claim 9, wherein the organic solvent is one or more selected from the group consisting of pyridine, lutidine and tetrahydrofuran.

11. The liquid composition of claim 9, wherein the total concentration of the Ti complex, bis(dipivaloylmethanato) barium complex and bis(dipivaloylmethanato)-strontium complex, is 1–20% by weight.

12. A Ti complex represented by the following structural formula (II):

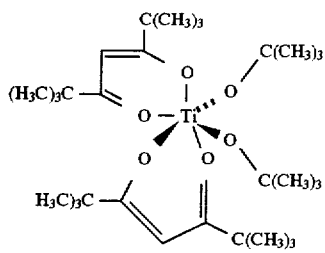

13. The Ti complex of claim 12, wherein said complex has an OH-group content of at most 0.1% by weight, and a chlorine content of at most 5 ppm.

14. A method of making cis-Ti(O-t-Bu)$_2$(DPM)$_2$ comprising:
   adding dipivaloylmethane to a solution of tetra-tert-butoxy-titanium in an organic solvent, thereby forming a mixture.

15. The method of claim 14, further comprising:
   heating the mixture to a temperature of 100° C. or higher, thereby removing residual chlorine and OH groups by azeotropy, and
   concentrating said mixture to form crystals.

16. The method of claim 14, wherein the tetra-tert-butoxy-titanium is dissolved in the organic solvent to a concentration of 1–70% by weight, the organic solvent is selected from the group consisting of aromatic hydrocarbons and aliphatic hydrocarbons, and the dipivaloylmethane is added to the solution in an amount 2.0–2.5 molar times that of the tetra-tert-butoxy-titanium.

17. The method of claim 15, wherein the crystals are recrystallized from an aprotic solvent selected from the group consisting of toluene, xylene and mesitylene.

18. A liquid composition comprising:
   a solution of the Ti complex of claim 12,
   one or more of bis(dipivaloylmethanato)-barium complex and bis(dipivaloylmethanato)-strontium complex, and
   an organic solvent.

19. The liquid composition of claim 16, wherein the organic solvent is one or more selected from the group consisting of pyridine, lutidine and tetrahydrofuran.

20. The liquid composition of claim 16, wherein the total concentration of the Ti complex, bis(dipivaloylmethanato)-barium complex and bis(dipivaloylmethanato)-strontium complex is 1–20% by weight.

* * * * *